United States Patent [19]

Tesmann et al.

[11] Patent Number: 4,891,154

[45] Date of Patent: Jan. 2, 1990

[54] DEFOAMING AGENTS AND PROCESS OF DEFOAMING

[75] Inventors: Holger Tesmann, Duesseldorf; Hans U. Hempel, Vilkerath; Heinz Mueller, Wuppertal-Vohwinkel; Margarete Gruenert, Kaarst; Adolf Asbeck, Duesseldorf, all of Fed. Rep. of Germany

[73] Assignee: Henkel Kommanditgesellschaft auf Aktien, Duesseldorf, Fed. Rep. of Germany

[21] Appl. No.: 59,170

[22] Filed: Jun. 11, 1987

Related U.S. Application Data

[63] Continuation of Ser. No. 603,400, Apr. 24, 1984.

[30] Foreign Application Priority Data

May 4, 1983 [DE] Fed. Rep. of Germany ....... 3316249

[51] Int. Cl.$^4$ ............................................. B01D 0/00
[52] U.S. Cl. .................................... 252/321; 256/351
[58] Field of Search ............... 556/446, 423, 419, 422, 556/437; 252/258, 321, 14.11, 351, 287.13, 287.16

[56] References Cited

U.S. PATENT DOCUMENTS

| | | |
|---|---|---|
| 3,935,133 | 1/1976 | van Leuwen et al. ............... 260/2.5 |
| 3,976,675 | 8/1976 | Scott et al. .......................... 556/446 |
| 4,051,053 | 9/1977 | Elliott et al. .................... 556/446 X |
| 4,093,554 | 6/1978 | Jayne et al. ..................... 556/446 X |
| 4,097,406 | 6/1978 | Scott et al. ........................... 252/351 |
| 4,141,851 | 2/1979 | Askew et al. ................... 556/446 X |
| 4,172,186 | 10/1979 | Scott et al. ...................... 556/446 X |
| 4,197,252 | 4/1980 | Joch et al. ........................... 556/446 |
| 4,467,105 | 8/1984 | Kötzsch et al. ................. 556/446 X |

FOREIGN PATENT DOCUMENTS 1644945 3/1974 Fed. Rep. of Germany .

OTHER PUBLICATIONS

Chemistry, Physics and Application of Surface Active Substances Proc. Int. Congress, 4th, 1964, vol. 1 (1967), pp. 199-207.
Noll, "Chemistry and Technology of Silicones", Academic Press, NY, (1968), p. 452.

*Primary Examiner*—Paul F. Shaver
*Attorney, Agent, or Firm*—Ernest G. Szoke; Wayne C. Jaeschke; Henry E. Millson, Jr.

[57] ABSTRACT

Substantially water-insoluble silicic acid esters corresponding to the following general formula

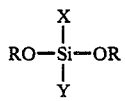

are used to foam inhibitors in foaming systems. In the above formula, X and Y represent the group —OR or a methyl group, R represents a polypropylene glycol ether group and, optionally, a polyethylene glycol ether group which may be substituted by alkoxyl, aminoalkyl, acyl, acylamino, dialkoxyl and oxyaminoalkyl groups containing from 4 to 24 carbon atoms. The total number of glycol ether groups amounts to between 1 and 100, the number of polypropylene glycol ether groups preferably being at least equal to or larger than the number of ethylene glycol ether groups.

21 Claims, No Drawings

DEFOAMING AGENTS AND PROCESS OF DEFOAMING

This application is a continuation of application Ser. No. 603,400, filed 4/24/84.

BACKGROUND OF THE INVENTION

This invention relates to the use of substantially water-insoluble silicic acid esters containing polypropylene glycol groups and, optionally, polyethylene glycol groups as foam inhibitors in foaming systems.

It is know that organopolysiloxanes, particularly in conjunction with silica aerogel, have foam-suppressing properties and, by virtue of those properties, are widely used as defoaming agents. However, their production is relatively complicated, so that there is an interest in more readily obtainable defoaming agents. In numerous fields of application, their strong hydrophobizing properties give rise to problems through undesirable surface effects. Their extremely high resistance to environmental influences can also be a disadvantage because, on the other hand, their foam suppressing properties are, in general, only briefly utilized, as for example in food production or papermaking, while on the other hand the period of time up to mineralization under environmental conditions is extremely long.

There has been no shortage of attempts to replace organopolysiloxanes by other substances having a comparable defoaming effect. In most cases, however, only partial solutions have been achieved, i.e. the substitutes only show a satisfactory effect in specific systems or in special applications, but frequently fail in the event of changes in the conditions under which they are used. Accordingly, there is still a considerable interest in universally useable foam inhibitors which are not attended by any of the disadvantages mentioned above.

On the other hand, silicic acid esters from compounds containing polyglycol ether groups are known. Orthosilicic acid esters of water-soluble, ethoxylated, relatively high-molecular-weight alcohols and alkyl phenols, which are suitable for use as pigment dispersants in aqueous media, are described in "Chemistry, Physics and Application of Surface Active Substances", Proc. Int. Congr. 4th 1964, Vol. 1 (1967), pages 199 to 207. There is no mention of any foam-inhibiting effect. Neither would such an effect be attributed to compounds such as these on account of their relatively high solubility in water. German No. 1,644,945 describes orthosilicic acid esters of polyethylene glycol and butyl polyethylene glycol and also their use as hydraulic oils. There is no reference to their use as form inhibitors. Finally, U.S. Pat. Nos. 3,935,133 and 4,097,406 describe reaction products of silicon tetrachloride with alcohols and partial replacement of the alcoholate with mono-lower alkyl ethers of ethylene oxide-propylene oxide block polymers which are used as stabilizers in the production of polyurethane foams. There is no indication in either of these two patents that compounds of this type have a foam-inhibiting effect.

OBJECTS OF THE INVENTION

An object of the present invention is the development of substantially water-insoluble silicic acid esters having the formula

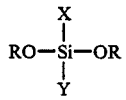

wherein X and Y, independently, are selected from the group consisting of methyl and —OR and R represents a polypropylene glycol ether group, optionally containing polyethylene glycol ether groups, which may be substituted, for use as foam inhibitors in foaming systems.

Another object of the present invention is the obtaining of a substantially water-insoluble silicic acid ester having the formula

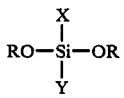

wherein X and Y, independently, are selected from the group consisting of methyl and —OR and R is a polypropylene glycol ether, optionally containing polyethylene glycol ether groups, which optionally may be terminally substituted.

A further object of the present invention is the development of a process for the production of a substantially water-insoluble silicic acid ester consisting essentially of the steps of reacting a silane having the formula

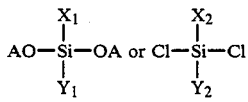

where A represents a $C_{2-7}$-alkyl, $X_1$ and $Y_1$ independently, are selected from the group consisting of methyl and —OA, and $X_2$ and $Y_2$, independently, are selected from the group consisting of methyl and Cl, with an alkoxylated alcohol selected from the group having the following formulae

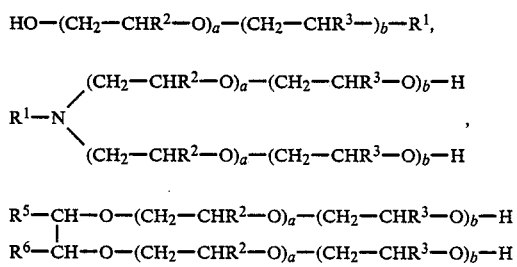

-continued

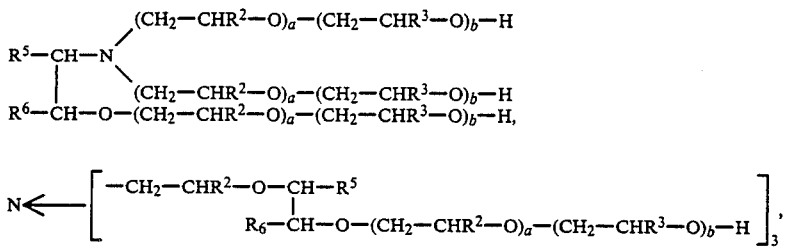

and

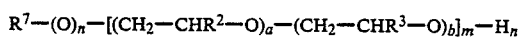

wherein $R^1$ is selected from the group consisting of hydrogen, $C_{4-24}$-alkyl, unsaturated $C_{4-24}$-hydrocarbyl, $C_{4-24}$-alkanoyl, unsaturated $C_{4-24}$-hydrocarboyl and $C_{4-14}$-alkylphenol; $R^2$ and $R^3$, independently, are selected from the group consisting of hydrogen and $CH_3$, where at least one of $R^2$ or $R^3$ is $CH_3$; one of $R^5$ or $R^6$ is a $C_{1-14}$ hydrocarbyl and the other of $R^5$ or $R^6$ is selected from the group consisting of hydrogen and $C_{1-24}$-hydrocarbyl, where the total number of carbon atoms present in $R^5$ and $R^6$ is between 6 and 22; $R^7-(O)_n$ is the residue of a polyol having from 3 to 24 carbon atoms, a and b are integers from 0 to 100 with the proviso that the sum of a and b is between 2 and 100; m is an integer equal to or less than n, but at least 2 and n is an integer corresponding to the number of hydroxyl groups in said $R^7-(O)_n$; in at least stoichiometrical molar ratio of the alcohol to the number of alkoxy or chloro groups in said silane at elevated temperatures with removal or the low molecular weight alcohol or hydrogen chloride produced, and recovering said substantially water-insoluble silicic acid ester.

These and other objects of the invention will become more apparent as the description thereof proceeds.

DESCRIPTION OF THE INVENTION

The present invention, by which the problem stated at the beginning is solved, relates to the use of silicic acid esters corresponding to the following general formula

in which X and Y independently of one another represent a methyl group or the radical —O—R and the symbols R represent polyglycol ether radicals optionally containing other, $C_4$-$C_{24}$ substituents, as foam inhibitors in foaming systems.

The silicic acid esters are derived from the following configurations:

Si (OR)$_4$      (Ia)

CH$_3$Si (OR)$_3$      (Ib)

(CH$_3$)$_2$Si (OR)$_2$      (Ic)

It is preferred to use the silicic acid esters of formula Ia which are distinguished from those of formulae Ib and Ic by greater activity.

The component R may be selected, for example, from the following groups of compounds:

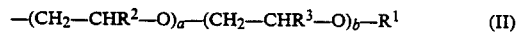      (II)

in which $R^1$ represents a saturated or unsaturated linear or branched hydrocarbyl or hydrocarboyl radical containing from 4 to 24 and preferably from 6 to 20 carbon atoms or an alkylphenyl radical containing a linear or branched $C_4$-$C_{14}$-alkyl radical, $R^2$ and $R^3$ independently of one another represent hydrogen or a $CH_3$-group and a and b represent integers, with the proviso that their sum amounts to between 2 and 100, the alkoxylates either exclusively containing propylene glycol ether groups or a combination of propylene glycol ether groups with ethylene glycol ether groups. In compounds containing both ethylene glycol ether groups (EO) and also propylene glycol ether groups (PO) (one of the two radicals $R^2$ and $R^3$ represents hydrogen while the other represents $CH_3$), the number of EO-groups present in a radical $R^1$ preferably amounts to between 1 and 20 and, more particularly, to between 2 and 15 and the corresponding number of PO-groups preferably amounts to between 1 and 30 and, more particularly to between 3 and 25, the number of PO-groups preferably being equal or greater than the number of EO-groups in the interests of reduced solubility in water. In compounds exclusively containing PO-groups ($R^2=CH_3$, b=O), the index a preferably has a value of from 3 to 30 and, more particularly, a value of from 4 to 20.

The alkyl or acyl radicals $R^1$ may be derived from naturally occurring or synthetic fatty residues, for example mixtures of naturally occurring fatty acids or of the fatty alcohols derived therefrom, for example based on coconut oil, palm kernel oil, tallow, rapeseed oil, train oil or tall oil fatty acids. Suitable synthetic compounds are, for example, oxo-alcohols. Compounds containing branched alkyl radicals, such as Guerbet alcohols, for example 2-ethyl hexanol, 2-butyl octanol and 2-hexyl decanol, are also suitable. Finally, residues containing different hydrocarbon radicals and having a different degree of alkoxylation or a different structure of the polyglycol ether radicals, may also be present in one and the same molecule.

Other suitable starting materials for the component R are di- and polyfunctional compounds containing hydroxyl groups. These compounds may contain relatively long-chain hydrocarbon radicals which may correspond in structure and composition to those of $R^1$ (see above). The examples include alkoxylated alkylamines corresponding to the following formula

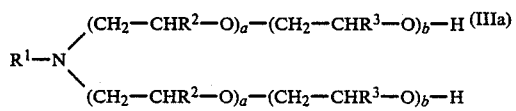 (IIIa)

and acylamides corresponding to the following formula

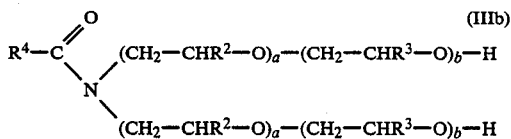 (IIIb)

in which $R^1$, $R^2$, $R^3$ and the parameters a and b are as defined above while $R^4$ represents the radical $R^1$ reduced by one $CH_2$-group, where $R^1$ is not an acyl group.

Other polyfunctional components containing relatively long chain hydrocarbon radicals are alkoxylation products of diols corresponding to the following formula

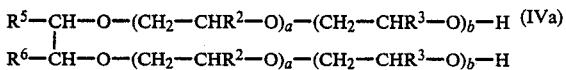 (IVa)

of hydroxyalkylamines corresponding to the following formula

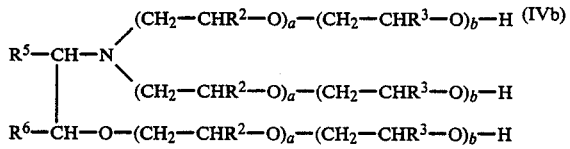 (IVb)

and of derivatives of trialkanolamine corresponding to the following formula

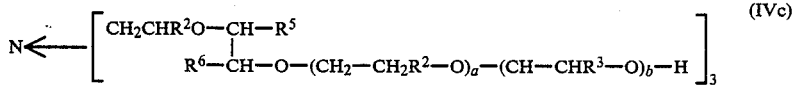 (IVc)

in which $R^2$, $R^3$, a and b are as defined above and at least one of the radicals $R^5$ and $R^6$ is a hydrocarbon radical containing from 1 to 24 carbon atoms while the other radical represents hydrogen or a hydrocarbon radical containing from 1 to 24 carbon atoms, with the proviso that the total number of carbon atoms present in $R^5$ and $R^6$ amounts to between 6 and 22. The above-mentioned components may be obtained, for example, by reacting $C_6-C_{24}$-epoxides with water, ethylene or propylene glycol (IVa) or alkanolamines, followed by alkoxylation.

With regard to the number of EO-groups and PO-groups, the same applies to the components of formulae III and IV as to the component of formula II so far as the desired reduced solubility in water is concerned.

Other di- and polyfunctional components are the alkoxylation products of polyols, such as glycerol, polyglycerol, trimethylol propane, pentaerythritol and sugar alcohols corresponding to the following formula:

$$R^7-(O)_n-[(CH_2-CHR^2-O)_a-(CH_2-CHR^3-O)_b]_m-H_n \quad (V)$$

in which $R^7-(O)_n$ represents a polyol radical containing from 3 to 24 carbon atoms, a+b=5 to 100, m is equal to or smaller than n in value, but amounts to at least 2, and n corresponds to the number of hydroxyl groups in the polyol. The number of PO-groups should be greater than the number of EO-groups. Components of formula V containing from 5 to 30 PO-groups and no EO-groups are particularly suitable.

Finally, other suitable difunctional components include polypropylene glycol having a molecular weight of from 400 to 6000 and preferably from 1600 to 3000, also block polymers of ethylene oxide and propylene oxide containing from 1 to 30 EO-groups and from 10 to 100 PO-groups, in which the number of PO-groups exceeds that of the EO-groups and preferably amounts to a multiple thereof.

The silicic acid esters are produced in known manner by reacting the corresponding silicon halides, particularly silicon tetrachloride, trichloromethyl silane or dichlorodimethyl silane, with the corresponding alcoholic components, the hydrogen halide given off during the reaction being removed. Where silicic acid esters, particularly tetraethoxy silane, triethoxy methyl silane or diethoxy dimethyl silane, are used as starting material, they are transesterfied with the alcoholic component, for example by heating a mixture of the reactants to 140°-180° C. with removal of the low molecular weight alcohol by distillation. The reaction may also be carried out in the presence of known transesterification catalysts.

Where di- or polyfunctional alcoholic components corresponding to formulae III, IV and V are polypropylene glycol ethers of blocked polymers of polyethylene glycol and polypropylene glycol are used, dimeric or oligomeric silicic acid esters may also be formed in addition to the monomeric esters, although the proportion in which they are formed amounts to less than 50% and generally to less than 30%, providing stoichiometric or overstoichiometric quantities are used, i.e. providing the alcoholic component is used in a ratio of 1 mol or more to one halogen function or ester function of the silicic acid residue. The dimeric or oligomeric esters, the presence of which is reflected in a higher viscosity of the products, do not differ significantly from monomeric esters in regard to their foam-inhibiting effect and, in certain cases, may even increase it. Even the excess of unreacted alcohol remaining in the product does not impair the form-inhibiting effect and, in certain cases, may even increase it.

The invention therefore also relates to a process for the production of a substantially water-insoluble silicic acid ester consisting essentially of the steps of reacting a silane having the formula

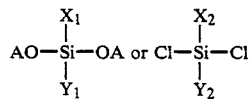

where A represents a $C_{2-7}$-alkyl, $X_1$ and $Y_1$, independently, are selected from the group consisting of methyl and —OA, and $X_2$ and $Y_2$, independently, are selected from the group consisting of methyl and Cl, with an alkoxylated alcohol selected from the group having the following formulae

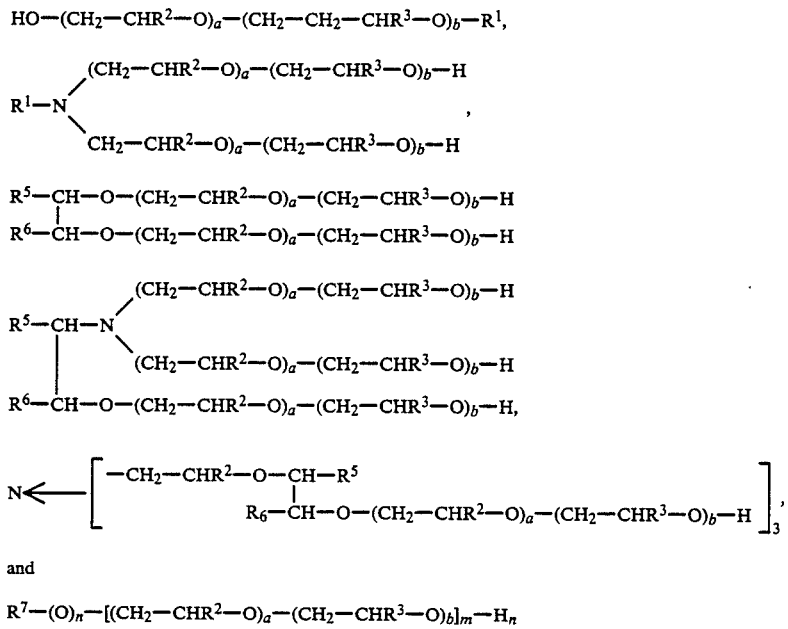

and $$R^7-(O)_n-[(CH_2-CHR^2-O)_a-(CH_2-CHR^3-O)_b]_m-H_n$$

wherein $R^1$ is selected from the group consisting of hydrogen, $C_{4-24}$-alkyl, unsaturated $C_{4-24}$-hydrocarbyl, $C_{4-24}$-alkanoyl, unsaturated $C_{4-24}$-hydrocarboyl and $C_{4-14}$-alkylphenol; $R^2$ and $R^3$, independently, are selected from the group consisting of hydrogen and $CH_3$, where at least one of $R^2$ or $R^3$ is $CH_3$; one of $R^5$ or $R^6$ is a $C_{1-24}$-hydrocarbyl, and the other of $R^5$ or $R^6$ is selected from the group consisting of hydrogen and $C_{1-24}$-hydrocarbyl, where the total number of carbon atoms present in $R^5$ and $R^6$ is between 6 and 22; $R^7$—$(O)_n$ is the residue of a polyol having from 3 to 24 carbon atoms, a and b are integers from 0 to 100 with the proviso that the sum of a and b is between 2 and 100; m is an integer equal to or less than n, but at least 2 and n is an integer corresponding to the number of hydroxyl groups in said $R^7$—$(O)_n$; in at least stoichiometrical molar ratio of the alcohol to the number of alkoxy or chloro groups in said silane at elevated temperatures with removal of the low molecular weight alcohol or hydrogen chloride produced, and recovering said substantially water-soluble silicic acid ester.

The above-mentioned silicic acid esters corresponding to formulae Ib and Ic are new chemical compounds. The silicic acid esters corresponding to formula Ia which are derived from components corresponding to formulae IIIa, IIIb, IVa, IVb, IVc and V and also from polypropylene glycol or from block polymers of polypropylene glycol and polyethylene glycol, are also new. The new compounds also include compounds corresponding to formula Ia in which the polyglycol ether groups consist exclusively of PO-groups or of PO-groups in combination with EO-groups. Even the compounds corresponding to formula I in which R consists of a butyl radical and the polyether glycol radicals consist of an EO-PO-block polymer are new in that the silicic acid moiety is monomeric, without presence of polymeric silicates.

Where they are new, the compounds are also included within the scope of the present invention. The silicic acid esters are suitable for use as foam inhibitors both for aqueous systems and also for non-aqueous systems. Accordingly, they are suitable for use in detergents and cleaners, in the paper industry, in glue production and also in the food industry and in biotechnology, for example for defoaming sugar-containing and protein-containing solutions and also ferment broths. They are also particularly suitable for defoaming aqueous and non-aqueous lacquer and paint systems and synthetic resin dispersions. They may also be used in the metal and petroleum industries, for example for defoaming drilling and cutting oils, mineral oils and oil dispersions. Depending on the particular application envisaged, they may be used either individually or in admixture with other known foam inhibitors in order further to optimize their performance properties.

Suitable additional foam inhibitors are, for example, paraffin oils and paraffins, including microcrystalline paraffins, fatty oils, such as triglycerides and partial glycerides, ester waxes, fatty alcohols and Guerbet alcohols and alkoxylation products thereof, polypropylene glycol and block polymers of polypropylene glycol with polyethylene glycol and monoalkyl ethers thereof, for example their monobutyl ether, or mono- and diesters thereof with saturated $C_{16}$–$C_{24}$-fatty acids or hydroxy fatty acids. Propoxylated glycerol or polyglycerol may also be used. Depending upon the proposed application and effect, the silicic acid esters may be used in quantities of from 0.001 to 3% by weight, based on the foaming substrate. In mixtures with other foam inhibitors, which are capable of intensifying the effect of, or partly replacing, the silicic acid esters, the proportion of the silicic acid esters may amount, for example, to between 1 and 50% by weight and the quantity used, based on the substrate, may even be further reduced.

The invention therefore also relates to the improvement in the process of defoaming a foaming system comprising adding to said foaming system a foam-inhibiting amount of a foam inhibitor and recovering a foaming system having substantially less foam, the improvement consisting of employing a substantially water-insoluble silicic acid ester having the formula

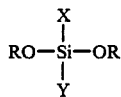

wherein X and Y, independently, are selected from the group consisting of methyl and —OR and R is a polypropylene glycol ether, optionally containing polyethylene glycol ether groups, which optionally may be terminally substituted, in a foam-inhibiting amount as said foam inhibitor.

The silicic acid esters are colorless to yellowish substances which, depending on the nature of the ester groups, are liquid to viscous and may even be of lard-like consistency. They may be emulsified in water by means of known emulsifiers, for example alkoxylated fatty alcohols or alkyl phenols, and used in that form. For certain applications, for example where they are used in detergents and cleaners, it may be advisable to apply them to a support, for example in the form of inorganic salts or adsorbents, or to embed them in microcapsules or to coat them with wax-like, water-soluble or water-dispersible organic materials to prevent interactions between the active constituents of the detergent or cleaner, such as tensicles or strong alkalis. They may even be dissolved or dispersed in organic solvents or mineral oils.

The following examples are illustrative of the invention without being limitative in any respect.

EXAMPLES

A number of the silicic acid esters described in the following was produced by mixing tetraethoxy silane (TES), triethoxy methyl silane (TMS) or diethoxy dimethyl silane (DDS) with the alcohol component in the molar ratio indicated and heating the resulting mixture under reflux with stirring for 2 hours in a nitrogen atmosphere to temperatures of from 150° to 160° C. The temperature was then increased to 175° C. and the ethanol given off during transesterification distilled off.

In cases where silicon tetrachloride (STC) was used as the starting material, the reaction was carried out by adding the STC dropwise to the alcohol component over a period of 30 minutes with vigorous stirring. After heating for 2 hours at 15 Torr, active carbon was added to the melts which were then filtered at room temperature using a filter aid.

The following alcohol components were used:

| | |
|---|---|
| A1 | nonylphenol + 9EO + 10PO |
| A2 | nonylphenol + 1EO + 1PO |
| A3 | $C_{12}$–$C_{14}$—fatty alcohol + 10PO |
| A4 | $C_{12}$–$C_{18}$—fatty alcohol + 5EO + 4PO |
| A5 | $C_{12}$–$C_{18}$—fatty alcohol + 5EO + 13PO |
| A6 | $C_{12}$–$C_{18}$—fatty alcohol + 2EO + 4PO |
| A7 | Isononanol + 10PO |
| A8 | isotridecanol + 2EO + 4PO |
| A9 | isotridecanol + 31PO |
| A10 | 2-ethylhexanol + 5PO |
| A11 | 2-hexyldecanol + 10PO |
| A12 | train oil fatty acid + 20PO |
| A13 | polypropylene glycol (MW = 2020) |
| A14 | block polymer of 1,2-propylene glycol + 30PO + 4.5EO |
| A15 | polyglycerol + 8PO |

A16 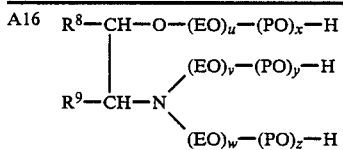

where $R^8$, $R^9$ = alkyl radicals containing a total of 9 to 11 carbon atoms (of internal vicinal epoxides)
  (a) u + v + w = 4
      x + y + z = 4
  (b) u + v + w = 4
      x + y + z = 10
  (c) u + v + w = 0
      x + y + z = 6
  (d) u + v + w = 0
      x + y + z = 12
  (e) u + v + w = 0
      x + y + z = 18
$R^8$, $R^9$ = alkyl radicals containing a total of 15 to 17 carbon atoms:
  (f) u + v + w = 0
      x + y + z = 10

A17 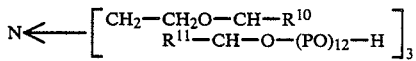

one of the two radicals $R^9$ and $R^{10}$ = $C_{12}$–$C_{14}$—alkyl, the other = hydrogen (from 1,2-epoxides)

A18 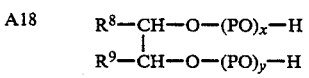

$R^8$ + $R^9$ = alkyl radicals containing a total of 9 to 11 carbon atoms
  (a) x + y = 9
  (b) x + y = 15
$R^8$ + $R^9$ = alkyl radicals containing a total of 13 carbon atoms
  (c) x + y = 9
  (d) x + y = 15

The molar ratios between the starting materials used (mol of Si compound to mol of alcohol component) are shown in Table 1, as is the Brookfield viscosity of the end products as measured at 22° C. In cases where silicon tetrachloride was used as starting material, a yield of more than 99.5% is calculated from the analytically determined chlorine content of 0.02% and less in the end product. A quantitative yield was also obtained where alkoxy silanes were used as starting material. It was only in cases where the product had been treated with active carbon and filtered that the yield was slightly less than quantitative on account of the losses occurring.

TABLE 1

| Example No. | Si-component | Alcohol component | Molar ratio | Viscosity mPa.s |
|---|---|---|---|---|
| 1 | STC | A1 | 1:4 | 470 |
| 2 | TES | A1 | 1:4.4 | 285 |
| 3 | TMS | A1 | 1:3.3 | 265 |
| 4 | STC | A2 | 1:4.4 | 4250 |
| 5 | STC | A3 | 1:5 | 120 |
| 6 | STC | A4 | 1:5 | 133 |
| 7 | STC | A5 | 1:5 | 252 |
| 8 | STC | A6 | 1:4.9 | 124 |
| 9 | STC | A7 | 1:5 | 110 |
| 10 | STC | A8 | 1:5 | 140 |
| 11 | STC | A9 | 1:5 | 285 |
| 12 | STC | A10 | 1:5 | 96 |
| 13 | STC | A11 | 1:5 | 202 |
| 14 | TES | A12 | 1:4 | 128 |
| 15 | TES | A13 | 1:4 | 510 |
| 16 | TES | A14 | 1:4 | 5000 |

TABLE 1-continued

| Example No. | Si-component | Alcohol component | Molar ratio | Viscosity mPa.s |
|---|---|---|---|---|
| 17 | TES | A15 | 1:8 | 3300 |
| 18 | TES | A16a | 1:4.4 | 5650 |
| 19 | TES | A16a | 1:4.6 | 3200 |
| 20 | TES | A16a | 1:4.7 | 2000 |
| 21 | TES | A16a | 1:5.1 | 1280 |
| 22 | TES | A16b | 1:5.1 | 4000 |
| 23 | TES | A16c | 1:3.8 | 9200 |
| 24 | TES | A16c | 1:4.2 | 2350 |
| 25 | TES | A16c | 1:4.6 | 1600 |
| 26 | TES | A16d | 1:4.6 | 6300 |
| 27 | TES | A16e | 1:5.1 | 4650 |
| 28 | TES | A16e | 1:5.6 | 660 |
| 29 | TES | A16f | 1:4.6 | 1340 |
| 30 | TMS | A16d | 1:3.4 | 1620 |
| 31 | DDS | A16d | 1:2.5 | 630 |
| 32 | TES | A17 | 1:5 | 3200 |
| 33 | TES | A18a | 1:4.2 | 1740 |
| 34 | TES | A18b | 1:4.2 | 4250 |
| 35 | TES | A18c | 1:4.2 | 2750 |
| 36 | TES | A18d | 1:4.2 | 4200 |

The defoaming agents were subjected to various performance tests. In a first series of tests, the following test solutions were used:

(A) An alkaline aqueous cleaning solution containing 15 g/l of sodium metasilicate, 0.2 g/l of dodecyl benzene sulfonate and 0.5 ml/l of a 10% solution of the defoaming agent in dioxane.

(B) An aqueous solution of 2 g/l of nonylphenol+-10EO+1ml/l of a 10% solution of the defoaming agent in dioxane (C) An aqueous solution of 2 g/l of di-tallow alkyl dimethyl ammonium chloride and 1 ml/l of a 10% solution of the defoaming agent in dioxane.

These tests were carried out at 25° C. using the method according to DIN 53 902. In this method, 200 ml of solution are introduced into a 1 liter capacity measuring cylinder. Foam generation is carried out by means of motor-driven perforated discs which are repeatedly immersed in and withdrawn from the solution. After 30 seconds (31 beats), the motor is switched off and the height of the column of foam measured after another 30 seconds. Measurement of the foam column is repeated at intervals of a few minutes. The results are set out in Table 2 in which the times indicated represent the time in minutes after switch off of the motor.

TABLE 2

| Ester of Example No. | Solution | Height of foam column after minutes | | | |
|---|---|---|---|---|---|
| | | 0.5 | 1 | 2 | 5 |
| 1 | A | 30 | 20 | 20 | 10 |
| 2 | | 20 | 20 | 20 | 10 |
| 3 | | 100 | 50 | 40 | 30 |
| 6 | | 40 | 30 | 30 | 20 |
| 8 | | 40 | 30 | 30 | 10 |
| 12 | | 30 | 20 | 20 | 10 |
| 13 | | 20 | 20 | 20 | 10 |
| 14 | | 20 | 20 | 10 | 10 |
| 15 | | 20 | 20 | 10 | 10 |
| 16 | | 40 | 40 | 30 | 20 |
| 17 | | 30 | 20 | 20 | 10 |
| — | | 180 | 180 | 180 | 160 |
| 8 | B | 70 | 70 | 60 | 30 |
| 12 | | 80 | 80 | 60 | 50 |
| 13 | | 30 | 20 | 20 | 20 |
| 14 | | 40 | 40 | 40 | 30 |
| 15 | | 30 | 20 | 20 | 10 |
| 16 | | 90 | 90 | 60 | 50 |
| — | | 380 | 380 | 380 | 380 |
| 2 | C | 130 | 90 | 70 | 60 |
| 8 | | 20 | 20 | 20 | 20 |
| 12 | | 100 | 80 | 80 | 60 |

TABLE 2-continued

| Ester of Example No. | Solution | Height of foam column after minutes | | | |
|---|---|---|---|---|---|
| | | 0.5 | 1 | 2 | 5 |
| 13 | | 40 | 30 | 30 | 20 |
| 14 | | 20 | 10 | 10 | 10 |
| 15 | | 20 | 10 | 10 | 10 |
| — | | 310 | 310 | 310 | 300 |

In a second series of tests, an aqueous solution D of 200 g/l of molasses was foamed by the "free-fall recirculation method". To this end, 500 ml of a 20% molasses solution are poured into a measuring cylinder (capacity 2 liters). By means of a laboratory peristaltic pump, this solution is continuously recirculated by being drawn in under suction from the bottom of the measuring cylinder under a glass tube and returned by free fall through a second glass tube flush with the upper edge of the measuring cylinder. For a recirculation rate of 4 liters per minute, a constant dynamic foam volume of 1800 to 2000 ml is obtained. Thereafter, 0.05 ml of a 10% solution of the defoaming agent to be tested are dropped onto the column of foam using a micropipette and the foam volumes and total volumes obtained are read off at intervals of 0.5, 1, 2, 3, 5, 10, 20 and 30 minutes. The defoaming agent is used in the form of a 10% solution in dioxane which, as an inert solvent, does not affect the foam.

TABLE 3

| Defoaming agent of Example No. | Height of foam after minutes | | | |
|---|---|---|---|---|
| | 0.5 | 1 | 2 | 5 |
| 2 | 620 | 620 | 640 | 760 |
| 5 | 600 | 620 | 640 | 720 |
| 14 | 600 | 660 | 680 | 720 |
| 16 | 540 | 580 | 600 | 720 |
| 17 | 600 | 620 | 620 | 700 |
| 26 | 540 | 540 | 580 | 640 |
| 34 | 550 | 560 | 600 | 680 |
| — | 1400 | 1600 | 1800 | 1800 |

Under the same test conditions, the other silicic acid esters listed in Table 1 showed similar foam values in solutions A to D. Only slight, gradual differences occurred.

In a third series of tests, the silicic acid esters were tested for their foam-inhibiting effect in gloss paints. In this particular field, it is crucially important that the formation of microfoams should be supressed because they can give rise to the formation of pores and craters in the dried paint film to the detriment both of gloss and of surface protection. The test paint used was an aqueous polyacrylate lacquer which as applied to panels of glass and wood by means of a sponge roller or sheepskin roller and assessed after drying. Assessment was based on a scale of 1 to 5 in which 1=very extensive inclusion of air
2=extensive inclusion of air
3=moderate inclusion of air
4=little inclusion of air
5=very little inclusion of air
6=no inclusion of air The following compositions specifically developed for paint systems of the type in question were used as the defoaming agents:

|  | E1 | E2 |
|---|---|---|
| Silicic acid ester or comparison substance | 14.0 | 6.0 |
| Mineral oil | 63.4 | 80.5 |
| Polypropylene glycol dibehenate | 9.0 | — |
| PO-EO-block polymer (30 PO, 4.5 EO) | 6.3 | — |
| Magnesium distearate | 2.7 | — |
| Aluminum stearate | 2.3 | 1.5 |
| Silica aerogel | — | 2.0 |
| Hydroxy stearyl monobehenate | — | 7.0 |
| Emulsifier (nonylphenol + 8 EO) | 2.3 | 3.0 |

The silicic acid esters of Examples 18 to 36 were used, two standard commercially available silicone defoaming agents being used for comparison. The following results were obtained:

| Example No. and comparison products | Film and surface assessment | Foam assessment |
|---|---|---|
| Examples 18–29 and 32–36 | foam free | 5 |
| Examples 30 and 31 | almost foam free | 4–5 |
| Silicone oil AK 10 | foam film | 1 |
| Silicone oil AK 6000 | foam film | 1 |
| Tetraethoxysilane | foam film | 1–2 |

In examples 30 and 31, very minor surface flow faults were observed, whereas flow faults were very pronounced in the comparison tests with silicon oils.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. In the process of defoaming an aqueous foaming system comprising adding to said aqueous foaming system a foam-inhibiting amount of a foam inhibitor and recovering an aqueous foaming system having substantially less foam, the improvement consisting of employing a substantially water-insoluble silicic acid ester having the formula $$\text{RO}-\underset{\underset{Y}{|}}{\overset{\overset{X}{|}}{\text{Si}}}-\text{OR}$$

wherein X and Y, independently, are selected from the group consisting of methyl or —OR and R is a polypropylene glycol ether containing at least three propylene glycol ether groups and optionally containing polyethylene glycol ether groups, which optionally may be terminally substituted, in a foam-inhibiting amount as said foam inhibitor.

2. The process of claim 1 wherein said polypropylene glycol ether, optionally containing polyethylene glycol ether groups is terminally substituted by a member selected from the group consisting of $C_{4-24}$-alkoxyl, $C_{4-14}$-aminoalkyl, $C_{4-24}$-acyl, $C_{4-24}$-acylamino, $C_{4-24}$dialkoxyl, $C_{4-24}$-Hydroxy-aminoalkyl and $C_{3-24}$-polyalkoxyl.

3. The process of claim 1 wherein the total number of glycol ether groups in R is between 1 and 100 and the number of propylene glycol ether groups is equal to or more than the number of ethylene glycol ether groups.

4. The process of claim 2 wherein the total number of glycol ether groups in R is between 1 and 100 and the number of propylene glycol ether groups is equal to or more than the number of ethylene glycol ether groups.

5. The process of claim 1 wherein R is a polypropylene glycol ether having a molecular weight of from 400 to 6000.

6. The process of claim 1 wherein R is a block polymer of propylene oxide and ethylene oxide containing from 1 to 30 ethylene glycol ether groups and from 10 to 100 propylene glycol ether groups with the proviso that the number of propylene glycol ether groups exceeds the number of ethylene glycol ether groups.

7. The process of claim 6 wherein said block polymer is terminally substituted by the process of claim 1 wherein said polypropylene glycol ether, optionally containing polyethylene glycol ether groups is terminally substituted by a member selected from the group consisting of $C_{4-24}$-alkoxyl, $C_{4-24}$-aminoalkyl, $C_{4-24}$-acyl, $C_{4-24}$-acylamino, $C_{4-24}$-dialkoxyl, $C_{4-24}$-Hydroxyaminoalkyl and $C_{3-24}$-polyalkoxyl.

8. A process for defoaming an aqueous foaming system comprising adding to said aqueous foaming system a foam-inhibiting amount of a substantially water-insoluble silicic acid ester foam inhibitor having the formula $$\text{RO}-\underset{\underset{Y}{|}}{\overset{\overset{X}{|}}{\text{Si}}}-\text{OR}$$

wherein X and Y, independently, are selected from the group consisting of methyl and —OR and R is a polypropylene glycol ether containing at least three propylene glycol ether groups and optionally containing polyethylene glycol ether groups, which optionally may be terminally substituted, and substantially reducing the foam height of said aqueous foaming system.

9. The process of claim 1 wherein said R polypropylene glycol ether, optionally containing polyethylene glycol ether groups is terminally substituted by a member selected from the group consisting of $C_{4-24}$-alkoxyl, $C_{4-24}$-aminoalkyl, $C_{4-24}$-acyl, $C_{4-24}$-acylamino, $C_{4-24}$-dialkoxyl, $C_{4-24}$-hydroxyaminoalkyl and $C_{3-24}$-polyalkoxyl.

10. The process of claim 1 wherein the total number of glycol ether groups in R is between 1 and 100 and the number of propylene glycol ether groups is equal to or more than the number of ethylene glycol ether groups.

11. The process of claim 9 wherein the total number of glycol ether groups in R is between 1 and 100 and the number of propylene glycol ether groups is equal to or more than the number of ethylene glycol ether groups.

12. The process of claim 8 wherein R is a polypropylene glycol ether having a molecular weight of from 400 to 6000.

13. The process of claim 8 wherein R is a block polymer of propylene oxide and ethylene oxide containing from 1 to 30 ethylene glycol ether groups and from 10 to 100 propylene glycol ether groups with the proviso that the number of propylene glycol ether groups exceeds the number of ethylene glycol ether groups.

14. The process of claim 13 wherein said block polymer is terminally substituted by a member selected from the group consisting of $C_{4-24}$-alkoxyl, $C_{4-24}$aminoalkyl, $C_{4-24}$-acyl, $C_{4-24}$acylamino, $C_{4-24}$-dialkoxyl, $C_{4-24}$-hydroxyaminoalkyl and $C_{3-24}$-polyalkoxyl.

15. The process of claim 8 wherein the silicic acid ester foam inhibitor is added to the foaming system in a foam inhibiting amount of 0.001 to 3% by weight based on the weight of the foaming system.

16. The process of claim 8 wherein the silicic acid ester foam inhibitor is added to an aqueous foaming system.

17. The process of claim 8 wherein the silicic acid ester foam inhibitor is added to an aqueous cleaning solution foaming system.

18. The process of claim 8 wherein the silicic acid ester foam inhibitor is added to an aqueous paint composition foaming system.

19. The process of claim 18 wherein the silicic acid ester foam inhibitor is added to an aqueous polyacrylate laquer paint composition foaming system.

20. The process of claim 8 wherein the silicic acid ester foam inhibitor is added to a non-aqueous paint composition foaming system.

21. The process of claim 8 wherein the silicic acid ester foam inhibitor is added to at least one of an oil or oil emulsion foaming system.

* * * * *